United States Patent
Takegami et al.

(10) Patent No.: US 7,900,473 B2
(45) Date of Patent: Mar. 8, 2011

(54) METHOD FOR ADIABATIC COOLING TYPE CRYSTALLIZATION OF ORGANIC COMPOUND AND APPARATUS THEREFOR

(75) Inventors: Keizo Takegami, Chuo-ku (JP); Junji Wakayama, Chuo-ku (JP); Kiwamu Ishii, Chuo-ku (JP)

(73) Assignee: Tsukishima Kikai Co., Ltd., Tokyo (JP)

( * ) Notice: Subject to any disclaimer, the term of this patent is extended or adjusted under 35 U.S.C. 154(b) by 738 days.

(21) Appl. No.: 11/887,243

(22) PCT Filed: Mar. 7, 2006

(86) PCT No.: PCT/JP2006/304329
§ 371 (c)(1),
(2), (4) Date: Sep. 26, 2007

(87) PCT Pub. No.: WO2006/112185
PCT Pub. Date: Oct. 26, 2006

(65) Prior Publication Data
US 2010/0192625 A1      Aug. 5, 2010

(30) Foreign Application Priority Data
Mar. 30, 2005   (JP) .................................. 2005-100172

(51) Int. Cl.
*B01D 9/04* (2006.01)
(52) U.S. Cl. ............................................. 62/534; 62/123
(58) Field of Classification Search .................... 62/534, 62/498, 123
See application file for complete search history.

(56) References Cited

U.S. PATENT DOCUMENTS
5,409,505 A * 4/1995 Morita et al. ................ 23/295 R
5,500,185 A * 3/1996 Cutler et al. .................... 422/16

FOREIGN PATENT DOCUMENTS
| DE | 972651 | 8/1959 |
| JP | 53-33551 | 9/1978 |
| JP | 03-042001 | 2/1991 |
| JP | 04-327542 | 11/1992 |
| JP | 05-309203 | 11/1993 |

* cited by examiner

*Primary Examiner* — Melvin Jones
(74) *Attorney, Agent, or Firm* — DLA Piper LLP (US)

(57) ABSTRACT

The present invention provides a method for adiabatic cooling type crystallization of organic compound and an apparatus therefore, by which running cost and facility cost can be reduced.

The method comprises carrying out adiabatic cooling and evaporation operation of a coolant in a crystallizer 20 for a mixture solution of a target organic compound containing the coolant; taking out crystal slurry produced by the operation from the crystallizer 20; pressurizing evaporated vapor to a pressure higher than the operation pressure in the crystallizer 20 by a compressor 30, introducing the vapor to an absorption condenser 10; cooling for condensation the mixture solution of organic compound and the evaporated vapor that has been pressurized while allowing them to contact each other in the absorption condenser 10; and introducing this absorption condensate to the crystallizer 20.

6 Claims, 2 Drawing Sheets

METHOD FOR ADIABATIC COOLING TYPE CRYSTALLIZATION OF ORGANIC COMPOUND AND APPARATUS THEREFOR

BACKGROUND OF THE INVENTION

1. Field of the Invention

The present invention relates to a method for adiabatic cooling type crystallization of organic compound and an apparatus therefore, and more particularly to a method and an apparatus suitable for obtaining paraxylene crystal.

2. Description of the Related Art

Separation and purification of a certain kind of isomer mixture are difficult in distillation operation because boiling points of components constituting the mixture are close to each other. However, there are many cases where melting points are largely different depending on the difference in molecular structures, and therefore, separation by crystallization operation is often effective.

There are methods of extractive and adductive crystallization in which a solvent-agent (extractant, additive) is added to a two-component eutectic system or a multi-component eutectic system as a third component; however, these are disadvantageous to recover the solvent-agent.

In this regard, a method in which a liquified gas component is used as a coolant is advantageous because its recovery is easy.

The present inventors have found that it is effective to carry out crystallization operation, with the use of propane (propene, ethylene, carbon dioxide, ammonia, or the like) as a direct injecting coolant, for a multi-component eutectic system such as xylene mixture (m-xylene+o-xylene+ethylbenzene+p-xylene system) that is a raw material for a typical p-xylene production in a petrochemical industrial process or a xylene mixture (m-xylene+o-xylene+p-xylene system) after isomerization reaction.

In this case, it is possible to carry out the crystallization operation in a jacket type crystallizer; however the crystallization is necessary to be carried out by cooling p-xylene in the multi-component eutectic system to about −30 degrees C. to −60 degrees C. Therefore, it is required to provide the crystallizer with a cooling surface scraper mechanics and a refrigeration unit by which the evaporated coolant from the jacket is compressed by a compressor, for example, under a high pressure of 20 atmospheres, followed by allowing this to be liquified and circulated to the jacket.

Using such a crystallizer results in not only an increase in power cost of the compressor but also increases in facility cost and maintenance cost because the crystallizer has to be provided with a cooling surface scraper mechanics that requires complex and frequent maintenance.

On the other hand, another system in which a heat pump is used is conceivable (Patent document 1: Japanese Patent Application Laid-Open Publication No. 1992-327542), but the system is not necessarily suitable in view of facility cost to construct the heat pump.

SUMMARY OF THE INVENTION

Main objects of the present invention are to provide a method for adiabatic cooling type crystallization of organic compound and an apparatus therefore in which running cost (including maintenance cost) and facility cost can be reduced.

Other objects of the present invention are to provide a method and an apparatus suitable for crystallization of p-xylene.

The present invention to solve the above problems is carried out as follows.

<Aspect According to Claim 1>

A method for adiabatic cooling type crystallization of organic compound comprising:

carrying out adiabatic cooling, as for crystallization operation of target organic compound and evaporation operation of a coolant which is directly introduced in crystallizer for a mixture solution of a target organic compound containing the coolant;

taking out crystal slurry produced by the operation from the crystallizer;

pressurizing evaporated vapor to a pressure higher than the operation pressure in the crystallizer by a compressor, introducing the pressurized coolant vapor to an absorption condenser, removing the heat of absorption and condensation, cooling the mixture solution of organic compound and the evaporated coolant vapor that has been pressurized, while allowing them to contact each other in the absorption condenser;

and introducing this absorption condensate to the crystallizer.

(Advantageous Effect)

When the adiabatic cooling and the evaporation operation of the coolant are carried out for the mixture solution of the target organic compound containing the coolant in the crystallizer, heat of crystallization is taken away in association with evaporation of substantially only the liquid coolant component, and crystal is crystallized. The evaporated vapor is pressurized to a pressure higher than the operation pressure in the crystallizer by the compressor and introduced to the absorption condenser for condensation. The reason why the evaporated vapor is pressurized to a pressure higher than the operation pressure in the crystallizer by the compressor is that a temperature difference for the condensation is generated as in the case of common refrigeration cycle, by pressurizing the evaporated vapor by the compressor. In the absorption condenser, since the evaporated vapor is brought into contact with the mixture solution of organic compound having a lower atmospheric pressure, the boiling point rises, thereby raising the temperature at which absorption and condensation can take place. Accordingly, a smaller degree of pressurization suffices the need, and a smaller energy input from outside suffices the need for the condensation.

Continuous crystallization operation can be carried out by introducing condensate liquid from the absorption condenser to the crystallizer. Taking crystallization of p-xylene as an example, propane is used as a coolant, the pressure in the crystallizer is, for example, normal atmospheric pressure, and the pressure in the absorption condenser is, for example, about eight atmospheric pressure by means of pressurization by the compressor. The crystal slurry produced in the crystallizer is taken out, separated into a crystal portion and mother liquid by a solid-liquid separation means. The crystal portion becomes a product as it is or after being purified by a purification means as necessary to enhance the purity. Since the target component remains in the mother liquid, it can be sent back to the crystallizer.

According to the above operation, crystallization operation is possible without constructing the crystallizer as a pressure resistant container. When at least a compressor and an absorption condenser are included as other necessary apparatuses, crystallization operation can be carried out, and therefore, an expensive structure installed with a refrigeration unit that was used in the prior art is not necessary, thus giving rise to an economical apparatus in view of entire system cost and running cost.

<Aspect According to Claim 2>

The method for adiabatic cooling type crystallization of organic compound according to claim 1, where the crystal slurry taken out from the crystallizer is subjected to solid-liquid separation, and the separated mother liquid is sent back to the absorption condenser.

(Advantageous Effect)

In the absorption condenser, not only is the mixture solution of organic compound supplied and brought into contact with the evaporated vapor that has been pressurized but also the crystal slurry taken out from the crystallizer is subjected to solid-liquid separation by a centrifuge, a liquid cyclone that is preferred in view of apparatus cost, or the like, and the separated mother liquid is sent back to the absorption condenser, thereby allowing it to come in contact with the evaporated vapor that has been pressurized. Which mode is to be selected can be determined depending on the kind of a target organic compound, concentration of the target organic compound in a feed mixture solution and operation conditions. Facilities and steps for the solid-liquid separation are not limited; however, for example, a centrifuge, a filter, a melt purification column, and a piston type or screw type wash column can be included.

<Aspect According to Claim 3>

The method for adiabatic cooling type crystallization of organic compound according to claim 1, where the operation pressure in the crystallizer is vacuum or equal to or lower than four atmospheric pressure.

(Advantageous Effect)

As to the operation pressure in the crystallizer (evaporation pressure), the operation is preferably carried out at around normal atmospheric pressure and at most at four atmospheric pressure when a pressure resistance property required for the crystallizer and the like, the separation method of produced crystal, and the apparatus are taken into consideration.

<Aspect According to Claim 4>

The method for adiabatic cooling type crystallization of organic compound according to claim 1, where the concentration of the coolant in the absorption condensate introduced from the absorption condenser to the crystallizer is set to from 1 to 70%.

(Advantageous Effect)

When the concentration of the coolant in the absorption condensate becomes higher, the crystallization point becomes lower, and the vapor pressure also becomes lower. When the concentration of the coolant in the absorption condensate becomes lower, the vapor pressure becomes lower in relation to the partial pressure. Accordingly, the highest point of the vapor pressure exists. When the concentration of the coolant in the absorption condensate is from 1 to 70%, the operation around the highest point of the vapor pressure is possible.

<Aspect According to Claim 5>

The method for adiabatic cooling type crystallization of organic compound according to claim 1, where the mixture solution of organic compound is a xylene mixture containing paraxylene, from which paraxylene crystal is obtained.

(Advantageous Effect)

The method is advantageous to obtain paraxylene crystal.

<Aspect According to Claim 6>

The method for adiabatic cooling type crystallization of organic compound according to claim 1, where the mixture solution of organic compound is a hexane mixture containing cyclohexane, from which cyclohexane crystal is obtained.

(Advantageous Effect)

The method is advantageous to obtain cyclohexane crystal.

<Aspect According to Claim 7>

An apparatus for adiabatic cooling type crystallization of organic compound comprising:

a crystallizer in which adiabatic cooling, crystallization and evaporation operation of a coolant are carried out for a mixture solution of a target organic compound containing the coolant;

a means to take out crystal slurry produced by the operation from the crystallizer;

a compressor that pressurizes evaporated vapor in the crystallizer to a pressure higher than the operation pressure in the crystallizer and introduces the vapor to an absorption condenser;

the absorption condenser that carries out condensation while bringing the mixture solution of organic compound into contact with the evaporated vapor that has been pressurized; and a means to introduce the absorption condensate to the crystallizer.

(Advantageous Effect)

The apparatus offers an advantageous effect similar to that of the aspect according to claim 1.

To summarize the effects described in the above sections of advantageous effect, cooling (crystallization) is possible in the facility for cooling crystallization without installing an unavoidable apparatus to scrape crystal that is crystallized on the cooling surface, and a necessary amount of energy consumed for the cooling can be reduced, thereby making it possible to reduce the running cost and facility cost. Further, the method and the apparatus are suitable for crystallization of p-xylene.

DETAILED DESCRIPTION

Hereinafter, exemplary embodiments of the present invention will be explained in detail.

First Embodiment

Figure 1:
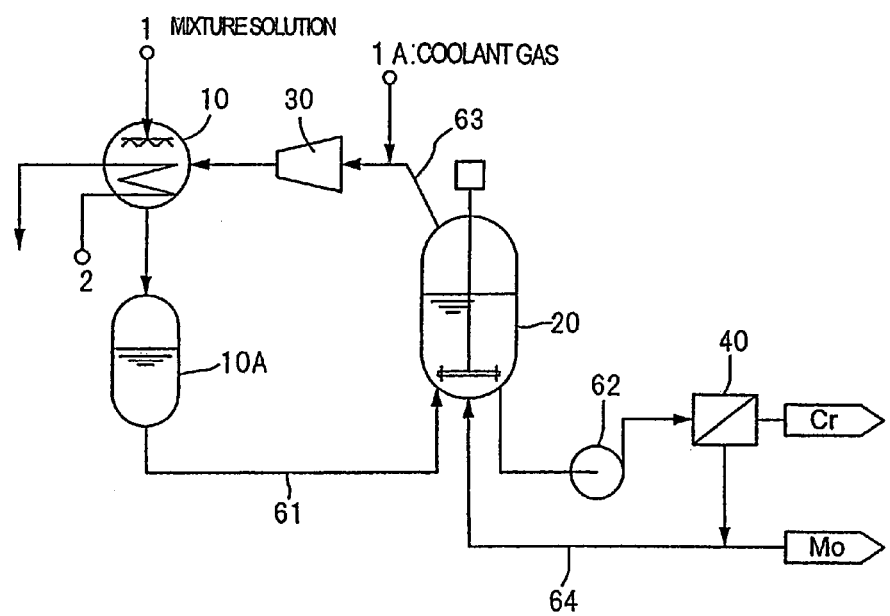
FIG. 1 is a flow sheet of a basic embodiment.

FIG. 1 represents a basic embodiment, which includes an absorption condenser 10, a crystallizer 20, a compressor 30, and a solid-liquid separation means 40.

A mixture solution 1 of a target organic compound containing a coolant (target liquid for crystallization operation, for example, a liquid of multi-component eutectic mixture containing p-xylene and its isomer) is introduced to the absorption condenser 10 and allowed to absorb coolant vapor (for example, propane) here to be condensed, making a homogeneous liquid mixed with the coolant. The liquid is introduced to the crystallizer 20 via a piping path 61 from a temporary storage tank 10A for absorption condensate, and adiabatic cooling and evaporation operation of the coolant is carried out for the condensed liquid containing the coolant in the crystallizer 20.

Crystal slurry produced by this operation is taken out from the crystallizer 20 by a pump 62 and separated into a flow of crystal portion Cr and a flow of mother liquid Mo by the solid-liquid separation means 40 such as centrifuge or liquid cyclone.

The evaporated vapor in the crystallizer 20 is allowed to pass a piping path 63, pressurized to a pressure higher than the operation pressure in the crystallizer 20 by the compressor 30, and introduced to the absorption condenser 10. While bringing the mixture solution of organic compound (mixture solution 1) into contact with the evaporated vapor that has been pressurized in the absorption condenser 10, absorption and condensation are carried out by cooling with cooling heat that a cooling medium 2 (for example, cooling water in cooling column or brine in freezer) has, and this absorption condensate is introduced to the crystallizer 20.

When adiabatic evaporation operation for the liquid coolant component is carried out, in the crystallizer 20, for the mixture solution of the target organic compound containing the liquid coolant component, crystallization heat is taken away in association with the evaporation of the liquid coolant component, and crystal is crystallized. The evaporated vapor is pressurized to a pressure higher than the operation pressure in the crystallizer 20 by the compressor 30 and introduced to the absorption condenser 10 to be subjected to absorption and condensation.

A temperature difference between the crystallizer 20 and the absorption condenser 10 that allows recondensation of the coolant at a temperature much higher than the operation temperature of the crystallizer 20 is secured by means of pressurization by the compressor 30.

In the absorption condenser 10, the evaporated vapor is brought into contact with the solution of the organic compound having high boiling points, and therefore the boiling point rises, thereby raising the temperature at which absorption and condensation can take place. Accordingly, a smaller energy input from outside suffices the need for absorption and condensation. It is possible to carry out continuous crystallization operation by introducing the absorption condensate in the absorption condenser 10 to the crystallizer 20. Taking crystallization of p-xylene as an example, propane is used as a coolant, the pressure in the crystallizer 20 is, for example, normal atmospheric pressure, and the pressure in the absorption condenser 10 is, for example, about eight atmospheric pressure by means of pressurization by the compressor 30. The crystal slurry produced in the crystallizer 20 is taken out, separated into the flow of crystal portion Cr and the flow of mother liquid Mo by a solid-liquid separation means. The flow of crystal portion Cr becomes a product as it is or after purification by a purification means as necessary as described later to enhance the purity. Since the target component remains in the flow of mother liquid Mo, part of the flow of mother liquid Mo can be sent back to the crystallizer 20 via a piping path 64 in order to enhance the recovery rate of the crystal of the target component.

According to the operation, crystallization operation is possible without constructing the crystallizer 20 as a pressure resistant container. When at least the compressor 30 and the absorption condenser 10 are included as necessary apparatuses, crystallization operation can be carried out, and therefore, an expensive structure installed with a refrigeration system that was used in the prior art is not necessary, thus giving rise to an economical apparatus in view of entire system cost and running cost.

Second Embodiment

Figure 2:
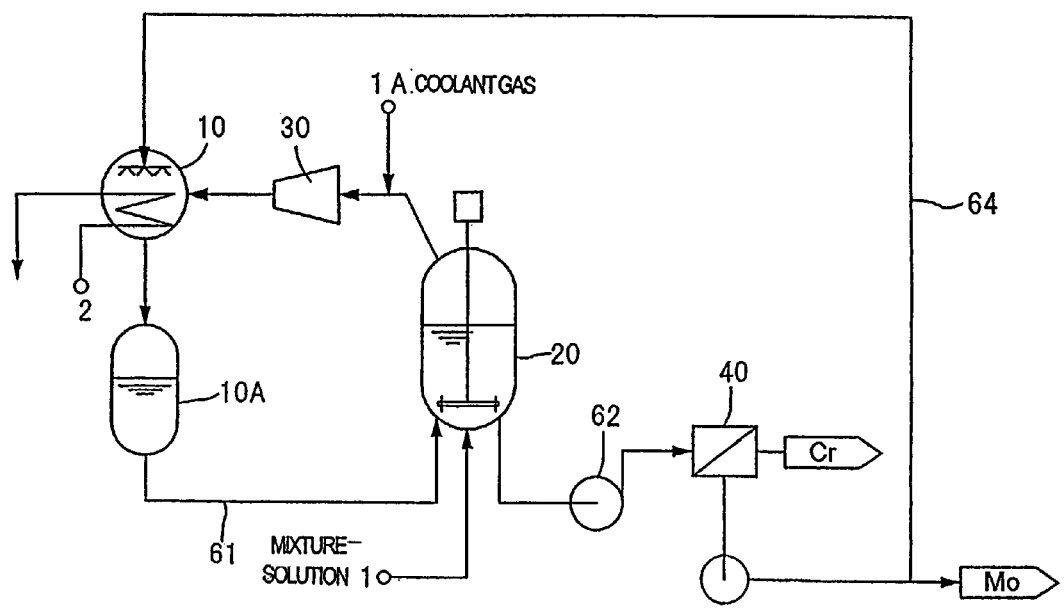
FIG. 2 is a flow sheet of another embodiment.

FIG. 2 represents a second embodiment. The crystal slurry taken out from the crystallizer 20 is subjected to solid-liquid separation by the solid-liquid separation means 40, and the separated flow of mother liquid Mo is sent back to the absorption condenser 10 via the piping path 64. The coolant in the portion discharged to the outside of the system in a state that the coolant is dissolved in the filtrate obtained by the solid-liquid separation means 40 can be recovered by the distillation column in the subsequent stage or supplied to a suction means of the compressor 30 as make-up (refer to FIG. 1, too).

For solid-liquid separation, a centrifuge, a filter, a cyclone, or the like can be used.

The initial mixture solution 1 of organic compound may be directly supplied to the crystallizer 20.

<Explanation of a Method for Crystallization>

Taking a benzene-cyclohexane system as an example, the method for crystallization is explained.

In common production in chemical industry, cyclohexane is produced by hydrogenation of benzene.

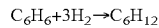

$$C_6H_6 + 3H_2 \rightarrow C_6H_{12}$$

In this hydrogenation reaction, the following impurities are produced by side reactions.

Methylcyclopentane
n-hexane
n-pentane
methylcyclohexane

In addition to these, toluene and paraffins contained in the raw material benzene are included.

In such a case, what is the most difficult in obtaining cyclohexane with high purity is that it becomes almost impossible to separate cyclohexane by distillation when unreacted benzene is contained. The boiling point of benzene at normal atmospheric pressure is 80.75 degrees C., and that of cyclohexane is 80.16 degrees C. The difference between them is only 0.59 degree C. Further, the lowest azeotropic point (77.62 degrees C.) is around 54 mol % of cyclohexane.

Figure 3:
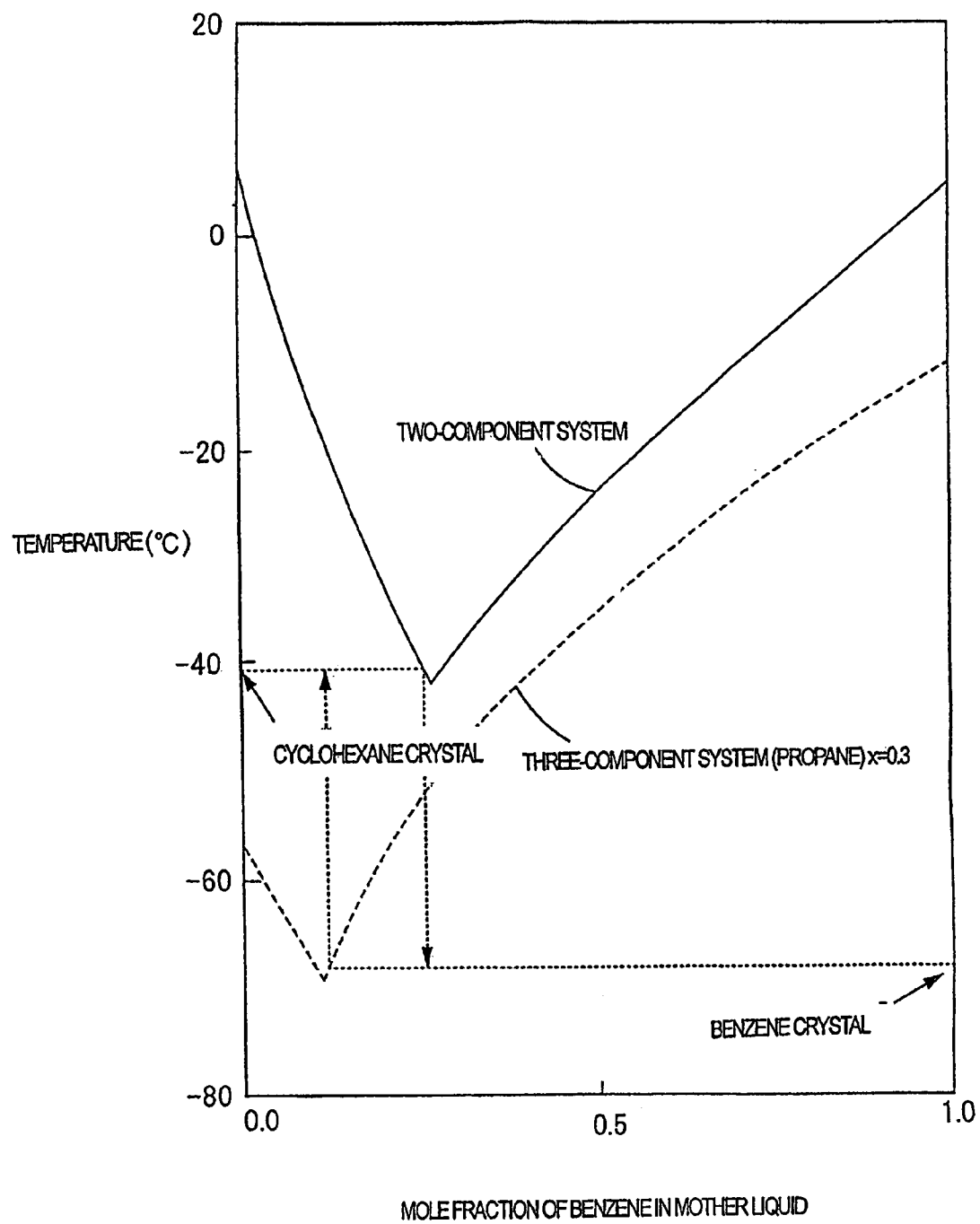
FIG. 3 is a solid-liquid equilibrium diagram of a eutectic composition of propane-benzene-cyclohexane system.

On the other hand, as is clear from the solid-liquid equilibrium diagram of a eutectic composition of propane-benzene-cyclohexane system shown in FIG. 3, a method of separation and purification by crystallization can be adopted when cyclohexane with high purity is desired to be obtained. In this method, it becomes possible to remove impurities such as methylcyclopentane contained together in a small amount at the same time.

In other words, in the phase diagram, a solid-liquid equilibrium line of the two-component system consisting of cyclohexane and benzene can be obtained. The content of impurities in a very small amount only slightly lowers the crystallization point curve, and there is no large substantial difference. When it is intended here that a mixed raw material rich in cyclohexane is cooled to crystallize cyclohexane, crystallization starts when the temperature reaches the solid-liquid line on the left side. Next, in the method for adiabatic cooling using propane, when a supply liquid and propane are mixed and cooling is started by releasing the pressure, crossing the solid-liquid equilibrium line (the line is drawn as component without propane) of the three-component system having added propane takes place. When cooling the liquid along the line to near the eutectic point, crystal of cyclohexane is crystallized, and this crystal is separated from the mother liquid.

Such operation is continuously carried out in the facility structure according to the present invention. The mother liquid separated from the cyclohexane crystal is subjected to propane removal, mixed with the raw material, and fed back. Note that a mixed liquid system of benzene and cyclohexane is a eutectic system in the range of all concentrations. The crystallization point of pure benzene is 5.5 degrees C. and that of cyclohexane is 5.7 degrees C.

From the explanation of this principle, it will be obvious that cyclohexane crystal can be obtained from a eutectic composition of propane-benzene-cyclohexane system. Further, according to the present invention, it will be also clear that a low cost crystallization process is provided for their separation.

<Other Explanations>

The above embodiments are examples in which one crystallizer is used. However, the present invention also aims at a structure provided with a plurality of crystallizers. In a facility provided with a plurality of crystallizers, crystal slurry in a crystallizer in a previous stage is introduced to a crystallizer in the subsequent stage, followed by carrying out further crystallization.

In this mode, a structure in which one compressor is provided, and evaporated vapor from the crystallizer in each stage is collectively introduced to the compressor and pressurized, followed by being introduced to the absorption condenser provided to a crystallizer in the final stage is more preferable than a case where a compressor is provided to each crystallizer in every stage.

Example 1

Hereinafter, the effects of the present invention are made clear by showing examples.

In the following example, crystallization was carried out by the process shown in FIG. 1. An vertical crystallizer (300 millimeter diameter×1.5 meter height, slurry hold-up capacity of 25 liters) was used as the crystallizer 20, and a horizontal tube type absorption condenser was used for the absorption condenser 10, and a centrifuge was used as the solid-liquid separation means 40. The numerical number 30 represents a compressor for vapor, and 10A represents a temporary storage tank for absorption condensate.

A raw material of xylene mixture having 80 to 90% paraxylene concentration at normal temperature was supplied to the absorption condenser 10 at a rate of 15 to 25 kg/hr and condensed at about 30 degrees C. while being brought into contact with and mixed with the vapor pressurized to 0.2 to 0.7 megapascal (MPa) by passing through the compressor 30 from the crystallizer 20. The obtained condensed liquid was a solution of xylene mixture containing propane at a concentration of 10 to 30%. This solution was introduced to the crystallizer 20 being run at −10 to 0 degree C. under normal atmospheric pressure for crystallization. The paraxylene crystal slurry obtained by the crystallization was supplied to the centrifuge 40 from the crystallizer 20. As the result, xylene crystal could be obtained at 4 to 7 kg/hr. The filtrate that was the solution of xylene mixture containing propane was discharged to the outside of the system. The propane in the portion discharged to the outside of the system in a state that the propane was dissolved in the filtrate was supplied to the suction means of the compressor 30 as make-up. The concentration of paraxylene in the filtrate was 60 to 80%.

Example 2

In the example 1, the raw material of xylene mixture having 70 to 80% paraxylene concentration at normal temperature obtained as a filtrate from the centrifuge 40 was supplied to the absorption condenser 10 at a rate of 15 to 25 kg/hr and condensed at about 30 degrees C. while being brought into contact with and mixed with the vapor pressurized to 0.2 to 0.7 MPa by passing through the compressor 30 from the crystallizer 20. The obtained condensed liquid was a solution of xylene mixture containing propane at a concentration of 10 to 30%. This solution was introduced to the crystallizer 20 being run at −20 to −5 degrees C. under normal atmospheric pressure for crystallization. Paraxylene crystal slurry obtained by the crystallization was supplied to the centrifuge 40 from the crystallizer 20. As the result, xylene crystal could be obtained at 4 to 7 kg/hr. The filtrate that was the solution of xylene mixture containing propane was discharged to the outside of the system. The propane in the portion discharged to the outside of the system in a state that the propane was dissolved in the filtrate was supplied to the suction means of the compressor 30 as make-up. The concentration of paraxylene in the filtrate was 50 to 70%.

What is claimed is:

1. A method for adiabatic cooling type crystallization of organic compound comprising:
    carrying out adiabatic cooling, as for crystallization operation of target organic compound and evaporation operation of a coolant which is directly introduced in crystallizer for a mixture solution of a target organic compound containing the coolant;
    taking out crystal slurry produced by the operation from the crystallizer;
    pressurizing evaporated vapor to a pressure higher than the operation pressure in the crystallizer by a compressor, introducing the pressurized coolant vapor to an absorption condenser, removing the heat of absorption and condensation, cooling the mixture solution of organic compound and the evaporated coolant vapor that has been pressurized, while allowing them to contact each other in the absorption condenser;
    introducing this absorption condensate to the crystallizer;
    subjecting the crystal slurry taken out from the crystallizer to solid-liquid separation; and
    sending the separated mother liquid back to the absorption condenser.

2. The method for adiabatic cooling type crystallization of organic compound according to claim 1, wherein the operation pressure in the crystallizer is vacuum or equal to or lower than four atmospheric pressure.

3. The method for adiabatic cooling type crystallization of organic compound according to claim 1, wherein the concentration of the coolant in the absorption condensate from the absorption condenser is set to from 1 to 70%.

4. The method for adiabatic cooling type crystallization of organic compound according to claim 1, wherein the mixture solution of organic compound is a xylene mixture containing paraxylene, from which paraxylene crystal is obtained.

5. The method for adiabatic cooling type crystallization of organic compound according to claim 1, wherein the mixture solution of organic compound is a hexane mixture containing cyclohexane, from which cyclohexane crystal is obtained.

6. An apparatus for adiabatic cooling type crystallization of organic compound comprising:
    a crystallizer in which adiabatic cooling, crystallization and evaporation operation of a coolant are carried out for a mixture solution of a target organic compound containing the coolant;
    a means to take out crystal slimy produced by the operation from the crystallizer;
    a compressor that pressurizes evaporated vapor in the crystallizer to a pressure higher than the operation pressure in the crystallizer and introduces the vapor to an absorption condenser;

the absorption condenser that carries out condensation while bringing the mixture solution of organic compound into contact with the evaporated vapor that has been pressurized;

a means to introduce the absorption condensate to the crystallizer;

a means to subject the crystal slurry taken out from the crystallizer to solid-liquid separation; and a means to send the separated mother liquid back to the absorption condenser.

* * * * *